US012805832B2

(12) United States Patent
Ebata

(10) Patent No.: US 12,805,832 B2
(45) Date of Patent: Nov. 24, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 97 days.

(21) Appl. No.: 18/539,215

(22) Filed: Dec. 13, 2023

(65) Prior Publication Data

US 2024/0108307 A1 Apr. 4, 2024

Related U.S. Application Data

(63) Continuation of application No. PCT/JP2022/020305, filed on May 16, 2022.

(30) Foreign Application Priority Data

Jun. 24, 2021 (JP) ................................ 2021-105119

(51) Int. Cl.
*A61B 8/08* (2006.01)
*A61B 8/00* (2006.01)

(52) U.S. Cl.
CPC .......... *A61B 8/0833* (2013.01); *A61B 8/4254* (2013.01); *A61B 8/463* (2013.01); *A61B 8/54* (2013.01); *A61B 8/4488* (2013.01)

(58) Field of Classification Search
CPC ... A61B 8/0833; A61B 8/4245; A61B 8/4254; A61B 8/429; A61B 8/4427;
(Continued)

(56) References Cited

U.S. PATENT DOCUMENTS

2008/0228067 A1* 9/2008 Truyen .................... G06T 7/136 600/425
2012/0296771 A1 11/2012 Vincent et al.
(Continued)

FOREIGN PATENT DOCUMENTS

EP 3865070 A1 8/2021
EP 3865074 A1 8/2021
(Continued)

OTHER PUBLICATIONS

Tanabe 2016195748 (Year: 2016).*
(Continued)

*Primary Examiner* — Brooke Lyn Klein
(74) *Attorney, Agent, or Firm* — Studebaker Brackett PLLC

(57) ABSTRACT

To reliably specify the presence or absence of excrement from an ultrasound image. In an ultrasound diagnostic apparatus and a control method for an ultrasound diagnostic apparatus according to the present invention, an excrement information detection unit detects an excrement region from an ultrasound image, and an excrement specifying unit specifies the presence or absence of excrement based on a detection result of the excrement region. As a result, in a case where it is specified that excrement is present, an excrement information display unit highlight-displays the excrement region in the ultrasound image displayed on a monitor, and in a case where it is not specified that excrement is present within a predetermined period, a notification unit notifies a user of a message suggesting a change of an approach of an ultrasound probe during performing scanning.

25 Claims, 9 Drawing Sheets

(58) Field of Classification Search
CPC ......... A61B 8/4488; A61B 8/46; A61B 8/461; A61B 8/463; A61B 8/469; A61B 8/5223; A61B 8/54
See application file for complete search history.

(56) References Cited

U.S. PATENT DOCUMENTS

| | | | | |
|---|---|---|---|---|
| 2016/0095581 | A1 | 4/2016 | Yoneyama et al. | |
| 2016/0310110 | A1* | 10/2016 | Dodd | A61B 8/54 |
| 2018/0053300 | A1* | 2/2018 | Podilchuk | G06T 7/0016 |
| 2020/0077976 | A1* | 3/2020 | Hirai | A61B 8/58 |
| 2020/0345324 | A1 | 11/2020 | Matsumoto et al. | |
| 2021/0137489 | A1 | 5/2021 | Matsumoto | |
| 2022/0265242 | A1* | 8/2022 | Guraschi | A61B 8/0866 |

FOREIGN PATENT DOCUMENTS

| | | | |
|---|---|---|---|
| JP | 2016195748 | A * | 11/2016 |
| JP | 6162493 | B2 | 7/2017 |
| JP | 6592836 | B2 | 10/2019 |
| WO | 2020/044758 | A1 | 3/2020 |
| WO | 2020/068306 | A1 | 4/2020 |
| WO | 2020/075449 | A1 | 4/2020 |
| WO | 2020/075609 | A1 | 4/2020 |
| WO | 2021/099278 | A1 | 5/2021 |

OTHER PUBLICATIONS

International Search Report issued in PCT/JP2022/020305; mailed Aug. 9, 2022.

International Preliminary Report on Patentability (Chapter I) and Written Opinion of the International Searching Authority issued in PCT/JP2022/020305; issued Dec. 14, 2023.

The extended European search report issued by the European Patent Office on Sep. 11, 2024, which corresponds to European Patent Application No. 22828099.6-1122 and is related to U.S. Appl. No. 18/539,215.

Artur Bijos et al., "The usefulness of ultrasound examination of the bowel as a method of assessment of functional chronic constipation in children", Pediatric Radiology, vol. 37, No. 12, Oct. 19, 2007, pp. 1247-1252, Springer, doi: 10.1007/s00247-007-0659-y.

"Notice of Reasons for Refusal" Office Action issued in JP 2023-529689; mailed by the Japanese Patent Office on Apr. 14, 2026.

An Office Action mailed by the Japanese Patent Office on Sep. 29, 2026, which corresponds to Japanese Patent Application No. 2023-529389 and is related to U.S. Appl. No. 18/539,215.

* cited by examiner

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

This application is a Continuation of PCT International Application No. PCT/JP2022/020305 filed on May 16, 2022, which claims priority under 35 U.S.C. § 119(a) to Japanese Patent Application No. 2021-105119 filed on Jun. 24, 2021. The above applications are hereby expressly incorporated by reference, in their entirety, into the present application.

BACKGROUND OF THE INVENTION

1. Field of the Invention

The present invention relates to an ultrasound diagnostic apparatus having a function of specifying the presence or absence of excrement in an ultrasound image and an excrement property and a control method for the ultrasound diagnostic apparatus.

2. Description of the Related Art

In recent years, a technique of performing constipation diagnosis including evaluation of the presence or absence of excrement and evaluation of excrement properties such as hard excrement, soft excrement, and normal excrement by using an ultrasound image has been proposed.

On the other hand, the constipation diagnosis using an ultrasound image has not yet become fully widespread as a diagnosis method and an examination method. As a result, even a skilled person has difficulty in interpreting excrement in the ultrasound image. In addition, it is very difficult for an inexperienced person or an unskilled person to interpret the ultrasound image itself.

For example, JP6592836B discloses a diagnostic apparatus that can evaluate whether a state of excrement inside the large intestine is normal, hard excrement, gas accumulation, or soft excrement by using information from ultrasound echo signals obtained from the large intestine using ultrasound waves. In addition, JP6592836B discloses a diagnostic apparatus that obtains ultrasound image data of the large intestine using an echo signal and evaluates whether or not a state of excrement inside the large intestine is soft excrement in the ultrasound image data.

Further, although not related to detection of excrement, JP6162493B discloses an ultrasound diagnostic apparatus that sets a section direction of reference images such as CT images acquired by various medical image diagnostic apparatuses depending on a purpose of diagnosis of a subject and a type of an ultrasound probe to be used, displays an ultrasound image and the reference image by performing registration between the ultrasound image and the reference image using a position sensor attached to the ultrasound probe, and navigates the ultrasound probe to a position of a lesion.

SUMMARY OF THE INVENTION

By specifying the presence or absence of excrement and an excrement property based on analysis of the ultrasound image and displaying the excrement region and the excrement property information on a monitor, in constipation diagnosis using ultrasound images, it can be expected that the display will help an inexperienced person and an unskilled person to diagnose constipation.

However, in a case of specifying the presence or absence of excrement and an excrement property from an ultrasound image, it is often difficult to determine an excrement region and an excrement property. For example, in a case where a person (doctor) specifies the presence or absence of excrement from an ultrasound image, a high-brightness region in a lower portion, such as a bladder, a vagina, or a prostate, may be determined as excrement. In addition, in a case where a person specifies the presence or absence of excrement from an ultrasound image, a fact that there is an acoustic shadow under the high-brightness region, a fact that the high-brightness region has a crescent shape, and the like are also used as determination conditions.

However, similar structures are scattered in both a case where excrement is present and a case where excrement is not present, or the excrement may be unclear due to an influence of gas. As a result, due to variations in appearance and the like, in many cases, even a person often erroneously determines the presence or absence of excrement or cannot specify an excrement region. Further, even in a case where an excrement region is detected from an ultrasound image using artificial intelligence, an excrement region may not be detected from the ultrasound image.

Therefore, an object of the present invention is to provide an ultrasound diagnostic apparatus and a control method for an ultrasound diagnostic apparatus capable of reliably specifying the presence or absence of excrement from an ultrasound image.

In order to achieve the above object, according to an aspect of the present invention, there is provided an ultrasound diagnostic apparatus including: an ultrasound probe; a monitor;

an image generation unit that generates an ultrasound image based on a reception signal obtained by scanning an examination area of a subject with ultrasound beams using the ultrasound probe; a display control unit that displays the ultrasound image on the monitor; an excrement information detection unit that detects an excrement region from the ultrasound image; an excrement specifying unit that specifies a presence or absence of excrement based on a detection result of the excrement region; an excrement information display unit that highlight-displays the excrement region in the ultrasound image displayed on the monitor in a case where it is specified that the excrement is present; and a notification unit that notifies a user of a message suggesting a change of an approach of the ultrasound probe during performing the scanning in a case where it is not specified that the excrement is present within a predetermined period.

Here, preferably, the excrement information detection unit detects the excrement region from the ultrasound image by using at least one of template matching, machine learning using image feature amounts, or a deep learning model.

Further, preferably, the excrement specifying unit specifies that the excrement is present in a case where the excrement region is detected from an ultrasound image of one frame.

Further, preferably, the excrement specifying unit specifies that the excrement is present in a case where the excrement region is detected from ultrasound images of frames of a predetermined number or more among ultrasound images of a plurality of continuous frames.

Further, preferably, the excrement specifying unit performs identity determination to determine whether or not the excrement regions in ultrasound images of adjacent frames are the identical excrement region, and counts the number of frames of the ultrasound images in which the identical excrement region is detected, as the predetermined number of frames.

Further, preferably, the excrement specifying unit performs the identity determination for each of the excrement regions in a case where a plurality of the excrement regions are detected in an ultrasound image of one frame.

Further, preferably, the excrement information detection unit detects, for each frame of the ultrasound images, the excrement region and a probability that the excrement region is a region of excrement, and the excrement specifying unit specifies the presence or absence of the excrement by comparing a statistic value of the probabilities of ultrasound images of a plurality of frames with a threshold value.

Further, preferably, the excrement information detection unit detects, for each frame of the ultrasound images and for each pixel of the ultrasound image, a probability that the pixel is a pixel of excrement, determines whether or not the pixel is a pixel of the excrement by comparing the probability that the pixel is the pixel of the excrement with a first threshold value, and detects, as the excrement region, a collection of a plurality of pixels that are determined as pixels of the excrement, and the excrement specifying unit obtains, as an index value, a statistic value of the probabilities of all the pixels in the excrement region of an ultrasound image of one frame, and specifies the presence or absence of the excrement by comparing a statistic value of the index values of ultrasound images of a plurality of frames with a second threshold value.

Further, preferably, measurement of the predetermined period is started immediately after the scanning is started.

Further, preferably, measurement of the predetermined period is started immediately after examination of the examination area of the subject is started.

Further, preferably, the ultrasound diagnostic apparatus further includes a contact detection unit that detects whether or not the ultrasound probe is brought into contact with the examination area of the subject, and measurement of the predetermined period is started immediately after contact of the ultrasound probe with the examination area of the subject is detected.

Further, preferably, the ultrasound diagnostic apparatus further includes a movement detection unit that detects a presence or absence of a movement of the ultrasound probe, and only a time during which the movement of the ultrasound probe is detected is measured as the predetermined period.

Further, preferably, the movement detection unit detects the presence or absence of the movement of the ultrasound probe based on at least one of an image analysis result of the ultrasound image, a movement detection result obtained by a motion sensor provided in the ultrasound probe, or a pressure detection result by a pressure sensor provided in the ultrasound probe.

Further, preferably, the notification unit notifies a user of a message representing that the excrement is present in a case where it is specified that the excrement is present.

Further, preferably, the ultrasound diagnostic apparatus further includes an approach determination unit that determines the approach. The notification unit selects an approach different from the approach with which scanning is being performed from among a plurality of preset approaches in a case where it is not specified that the excrement is present within the predetermined period, and notifies a user of a message suggesting a change to an approach different from the approach with which scanning is being performed.

Further, preferably, the notification unit notifies a user of a message representing that the excrement is not present in a case where it is not specified that the excrement is present by all of the plurality of preset approaches.

Further, preferably, the excrement information detection unit further detects excrement property information of the excrement region from the ultrasound image. The excrement specifying unit further specifies an excrement property of the excrement region based on the excrement property information. The excrement information display unit highlight-displays the excrement region in the ultrasound image displayed on the monitor in a case where it is specified that the excrement is present and the excrement property is specified. The notification unit notifies a user of a message suggesting a change of the approach in a case where it is not specified that the excrement is present within the predetermined period or in a case where it is specified that the excrement is present but the excrement property is not specified.

Further, preferably, the excrement information detection unit detects, for each frame of the ultrasound images, a statistic value of brightness in the excrement region, and the excrement specifying unit obtains, for each frame of the ultrasound images, a first comparison result by comparing the statistic value of brightness in the excrement region with a third threshold value, and specifies the excrement property based on the first comparison result in ultrasound images of one frame or a plurality of frames. Alternatively, the excrement information detection unit detects, for each frame of the ultrasound images, a brightness ratio between the statistic value of brightness in the excrement region and a statistic value of brightness in a predetermined region around the excrement region, and the excrement specifying unit obtains, for each frame of the ultrasound images, a second comparison result by comparing the brightness ratio with a fourth threshold value, and specifies the excrement property based on the second comparison result in ultrasound images of one frame or a plurality of frames.

Further, preferably, the excrement information detection unit detects the excrement region and a probability that the excrement region is included in each of classes of the excrement properties, and the excrement specifying unit specifies a class having a highest probability among the classes of the excrement properties, as the excrement property of the excrement region.

Further, preferably, the excrement information detection unit detects, for each pixel of the ultrasound image, a probability that the pixel is included in each of classes of the excrement properties, determines, among the classes of the excrement properties, a class having a highest probability as a class of the pixel, and detects, as the excrement region, a collection of a plurality of pixels that are determined as pixels of excrement based on the classes of the pixels. The excrement specifying unit obtains a total area of the classes for each of the classes of the excrement properties, and specifies a class having a largest total area, as the excrement property of the excrement region.

Further, preferably, the excrement specifying unit specifies that the excrement is present in a case where the excrement region is detected from an ultrasound image of one frame and the excrement property of the excrement region detected from the ultrasound image of the one frame is specified.

Further, preferably, the excrement specifying unit specifies that the excrement is present in a case where the excrement regions are detected from ultrasound images of frames of a predetermined first number or more among ultrasound images of a plurality of continuous frames and the excrement properties of the excrement regions, which are detected from ultrasound images of frames of a predetermined second number or more among the ultrasound images of the frames of the predetermined first number or more, are the same.

Further, preferably, the excrement specifying unit performs identity determination to determine whether or not the excrement regions in ultrasound images of adjacent frames are the identical excrement region, and counts the number of frames of the ultrasound images in which the identical excrement region is detected, as the predetermined first number of frames and the predetermined second number of frames.

Further, preferably, the ultrasound diagnostic apparatus has at least two operation modes among a first operation mode in which both the presence or absence of the excrement and the excrement property are not specified, a second operation mode in which the presence or absence of the excrement is specified but the excrement property is not specified, and a third operation mode in which both the presence or absence of the excrement and the excrement property are specified. The ultrasound diagnostic apparatus further includes a mode switching unit that switches an operation mode to one operation mode among the at least two operation modes according to an instruction from a user.

Further, preferably, the statistic value is an average value, a weighted average value, or a median value.

Further, according to another aspect of the present invention, there is provided a control method for an ultrasound diagnostic apparatus, the method including: a step of generating, via an image generation unit, an ultrasound image based on a reception signal obtained by scanning an examination area of a subject with ultrasound beams using an ultrasound probe; a step of displaying, via a display control unit, the ultrasound image on a monitor; a step of detecting, via an excrement information detection unit, an excrement region from the ultrasound image; a step of specifying, via an excrement specifying unit, a presence or absence of excrement based on a detection result of the excrement region; a step of highlight-displaying, via an excrement information display unit, the excrement region in the ultrasound image displayed on the monitor in a case where it is specified that the excrement is present; and a step of notifying a user of, via a notification unit, a message suggesting a change of an approach of the ultrasound probe during performing the scanning in a case where it is not specified that the excrement is present within a predetermined period.

According to the present invention, in a case where it is specified that excrement is present, the excrement region is highlight-displayed in the ultrasound image displayed on the monitor. Therefore, the user can easily recognize the excrement region in the ultrasound image. Further, even in a case where it is not specified that excrement is present within the predetermined period, notification of a message suggesting a change of the approach is performed. Therefore, the user can change the approach according to the message, and thus the presence or absence of excrement can be reliably specified.

DESCRIPTION OF THE PREFERRED EMBODIMENTS

Hereinafter, an ultrasound diagnostic apparatus and a control method for an ultrasound diagnostic apparatus according to an embodiment of the present invention will be described in detail based on a preferred embodiment illustrated in the accompanying drawings.

Figure 1:
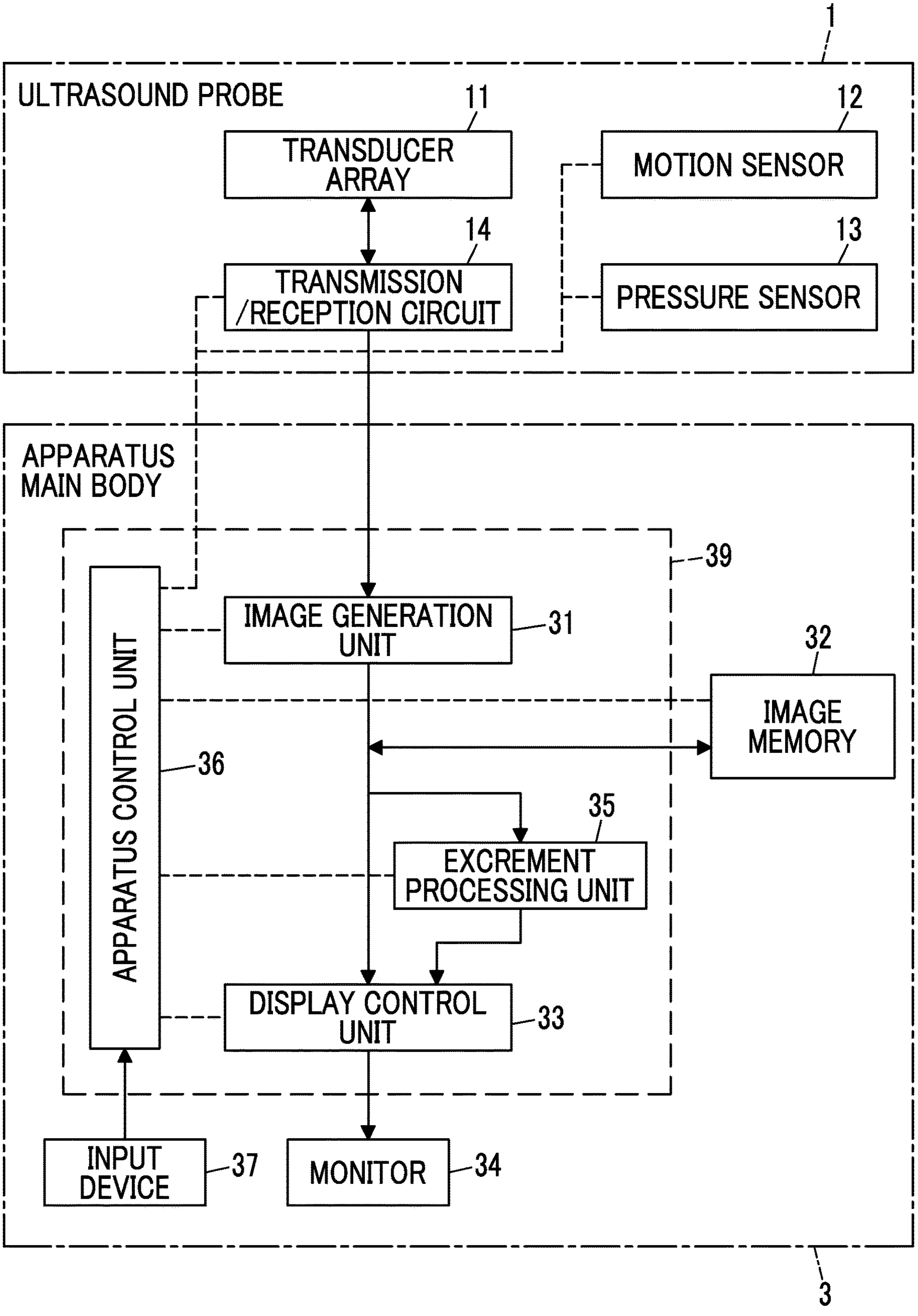
FIG. 1 is a block diagram of an embodiment illustrating a configuration of an ultrasound diagnostic apparatus of the present invention.

FIG. 1 is a block diagram illustrating a configuration of an ultrasound diagnostic apparatus according to an embodiment of the present invention. The ultrasound diagnostic apparatus illustrated in FIG. 1 is a stationary ultrasound diagnostic apparatus, and comprises an ultrasound probe 1, and an apparatus main body 3 connected to the ultrasound probe 1.

The ultrasound probe 1 scans an examination area of a subject with an ultrasound beam and outputs a sound ray signal corresponding to an ultrasound image of the examination area. As illustrated in FIG. 1, the ultrasound probe 1 comprises a transducer array 11, a transmission/reception circuit 14, a motion sensor 12, and a pressure sensor 13. The transducer array 11 and the transmission/reception circuit 14 are bidirectionally connected to each other. In addition, the transmission/reception circuit 14, the motion sensor 12, and the pressure sensor 13 are connected to an apparatus control unit 36 of the apparatus main body 3 to be described below.

The transducer array 11 includes a plurality of ultrasound transducers arranged one-dimensionally or two-dimensionally. In response to a drive signal supplied from the transmission/reception circuit 14, each of the transducers transmits an ultrasound wave, receives a reflected wave from the subject, and outputs an analog reception signal.

For example, each transducer is configured by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
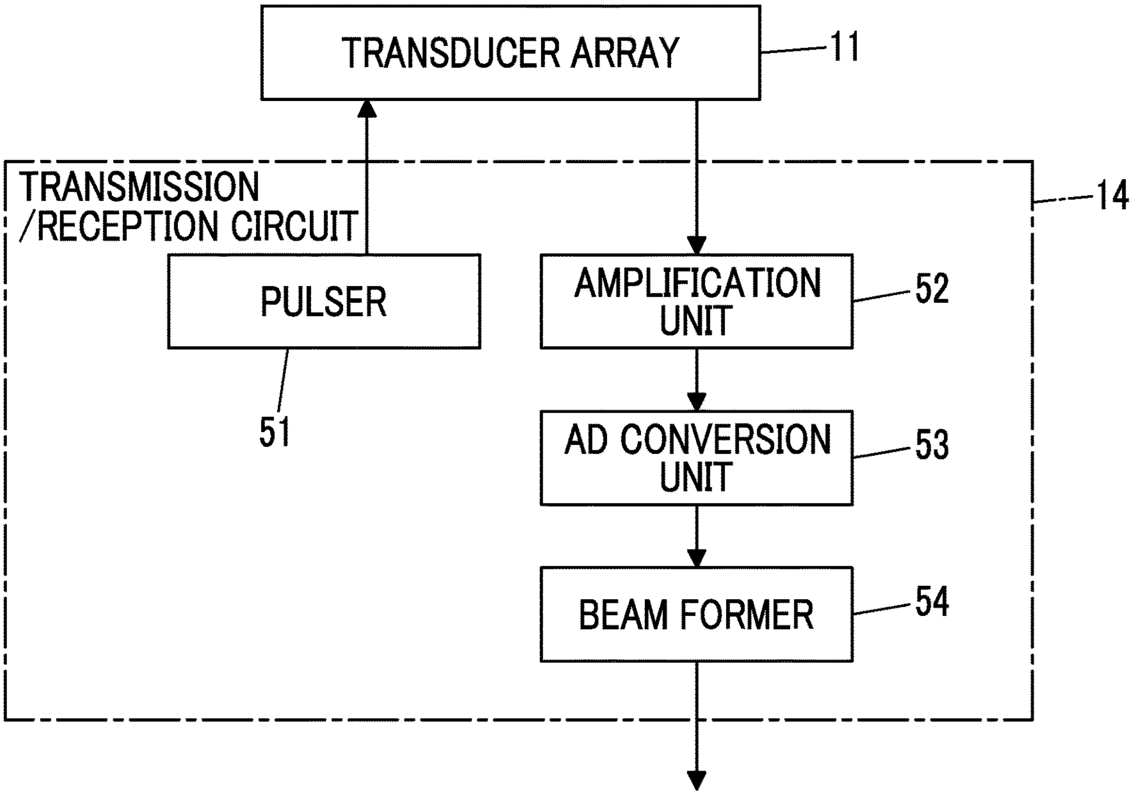
FIG. 2 is a block diagram of an embodiment illustrating a configuration of a transmission/reception circuit.

Under a control of the apparatus control unit 36, the transmission/reception circuit 14 causes the transducer array 11 to transmit an ultrasound wave, and performs reception focusing processing on the reception signal output from the transducer array 11 that receives an ultrasound echo. Thereby, a sound ray signal is generated. As illustrated in FIG. 2, the transmission/reception circuit 14 includes a pulser 51 connected to the transducer array 11, and an amplification unit 52, an analog-to-digital (AD) conversion unit 53, and a beam former 54 that are sequentially connected in series from the transducer array 11.

The pulser 51 includes, for example, a plurality of pulse generators. The pulser 51 adjusts a delay amount of each drive signal such that ultrasound waves transmitted from the plurality of transducers of the transducer array 11 form an ultrasound beam based on a transmission delay pattern selected by the apparatus control unit 36, and supplies the drive signals to the plurality of transducers. In this way, in a case where a voltage having a pulse shape or a continuous wave shape is applied to the electrodes of the transducers of the transducer array 11, the piezoelectric body expands and contracts. Thereby, ultrasound waves having a pulse shape or a continuous wave shape are generated from each transducer, and thus an ultrasound beam is formed from a composite wave of these ultrasound waves.

The transmitted ultrasound beam is reflected by, for example, a target such as a region of the subject, and propagates toward the transducer array 11 of the ultrasound probe 1. In a case where the ultrasound echo propagating toward the transducer array 11 in this way is received, each transducer of the transducer array 11 expands and contracts, and thus the reception signal that is an electric signal is generated. The reception signal is output to the amplification unit 52.

The amplification unit 52 amplifies the signals input from each transducer of the transducer array 11, and transmits the amplified signals to the AD conversion unit 53. The AD conversion unit 53 converts the analog signal transmitted from the amplification unit 52 into digital reception data, and outputs the reception data to the beam former 54.

The beam former 54 performs so-called reception focusing processing in which addition is performed by giving delays to each of pieces of the reception data converted by the AD conversion unit 53 according to a sound speed or a sound speed distribution which is set based on a reception delay pattern selected by the apparatus control unit 36. By this reception focusing processing, each of pieces of reception data converted by the AD conversion unit 53 is phase-added, and a sound ray signal in which the focus of the ultrasound echo is narrowed down is generated.

The motion sensor 12 detects the motion of the ultrasound probe 1.

The pressure sensor 13 detects a pressure applied to the ultrasound probe 1 in a case where the ultrasound probe 1 is brought into contact with the examination area of the subject.

Next, the apparatus main body 3 generates an ultrasound image of the examination area of the subject based on the sound ray signal generated by the ultrasound probe 1, and displays the ultrasound image of the examination area of the subject. As illustrated in FIG. 1, the apparatus main body 3 comprises an image generation unit 31, an image memory 32, an excrement processing unit 35, a display control unit 33, a monitor (display unit) 34, an input device 37, and the apparatus control unit 36.

The image generation unit 31 is connected to the transmission/reception circuit 14, and the display control unit 33 and the monitor 34 are sequentially connected to the image generation unit 31. In addition, each of the image memory 32 and the excrement processing unit 35 is connected to the image generation unit 31, and the display control unit 33 is connected to the image memory 32 and the excrement processing unit 35. The image generation unit 31, the display control unit 33, the image memory 32, and the excrement processing unit 35 are connected to the apparatus control unit 36, and the apparatus control unit 36 is connected to the input device 37.

Figure 3:
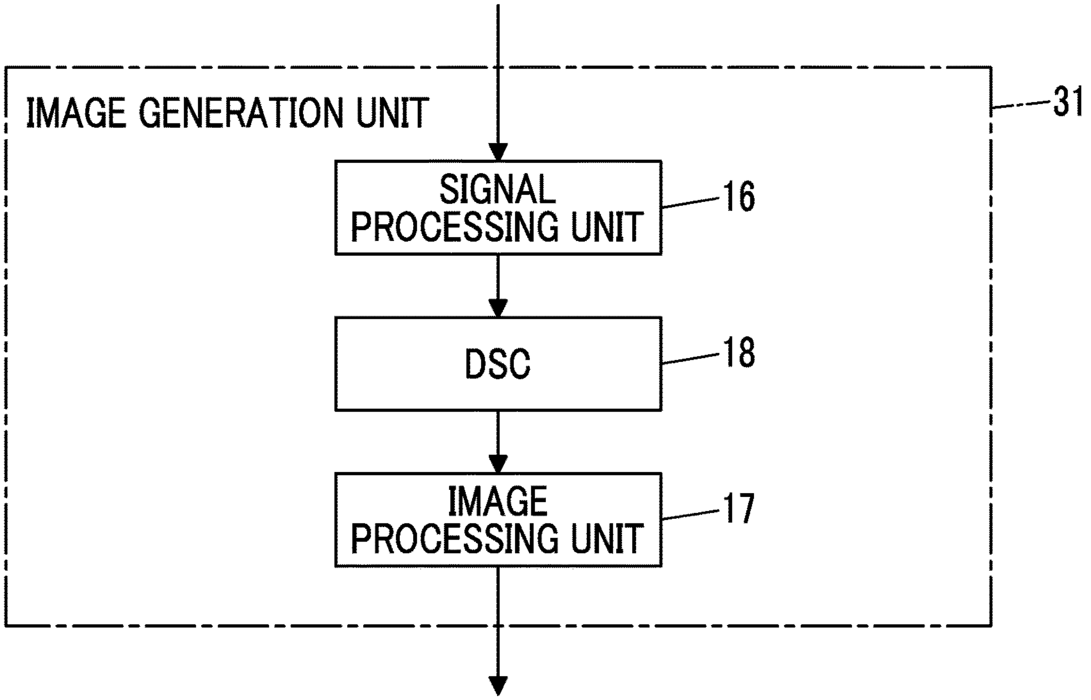
FIG. 3 is a block diagram of an embodiment illustrating a configuration of an image generation unit.

The image generation unit 31 generates an ultrasound image (ultrasound image signal) of the examination area of the subject, based on the reception signal obtained by scanning the examination area of the subject with the ultrasound beams by using the ultrasound probe 1 (more precisely, the transducer array 11), in other words, based on the sound ray signal generated from the reception signal by the transmission/reception circuit 14, under a control of the apparatus control unit 36. As illustrated in FIG. 3, the image generation unit 31 has a configuration in which a signal processing unit 16, a digital scan converter (DSC) 18, and an image processing unit 17 are sequentially connected in series.

The signal processing unit 16 generates image information data corresponding to the ultrasound image based on the sound ray signal generated by the transmission/reception circuit 14. More specifically, the signal processing unit 16 generates the image information data representing tomographic image information related to tissues inside the subject, by performing signal processing, for example, processing of correcting attenuation of the sound ray signal generated by the beam former 54 of the transmission/reception circuit 14, the attenuation being caused by a propagation distance according to a depth of the reflection position of the ultrasound wave, and then performing envelope detection processing.

The DSC 18 raster-converts the image information data generated by the signal processing unit 16 into an image signal according to a normal television signal scanning method.

The image processing unit 17 generates an ultrasound image (ultrasound image signal) by performing, on the image signal input from the DSC 18, various kinds of image processing such as brightness correction, gradation correction, sharpness correction, image size correction, refresh rate correction, scanning frequency correction, and color correction according to a display format of the monitor 34, and outputs the ultrasound image obtained by performing the image processing to the image memory 32, the excrement processing unit 35, and the display control unit 33.

The image memory 32 is a memory that stores ultrasound images (ultrasound image signals) of a series of a plurality of frames generated for each examination by the image generation unit 31, under a control of the apparatus control unit 36. Here, as the image memory 32, recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), an external server, or the like can be used.

The display control unit 33 displays various kinds of information on the monitor 34 under a control of the apparatus control unit 36. For example, the display control unit 33 performs predetermined processing on the ultrasound image generated by the image generation unit 31 or the ultrasound image stored in the image memory 32, and displays the processed ultrasound image on the monitor 34.

The monitor 34 displays various kinds of information under a control of the display control unit 33. The monitor 34 displays, for example, an ultrasound image or the like. Examples of the monitor 34 include a liquid crystal display (LCD), an organic electro-luminescence (EL) display, and the like.

The input device 37 receives various instructions input from the user (examiner) of the ultrasound diagnostic apparatus. The input device 37 is not particularly limited, and includes various buttons, a voice input device that inputs various instructions using voice recognition, a touch panel that allows a user to input various instructions by performing a touch operation on a graphical user interface (GUI) screen displayed on the monitor 34, and the like.

The apparatus control unit 36 controls the ultrasound probe 1 and each unit of the apparatus main body 3 based on a program stored in advance and an instruction or the like of the user that is input from the input device 37.

Figure 4:
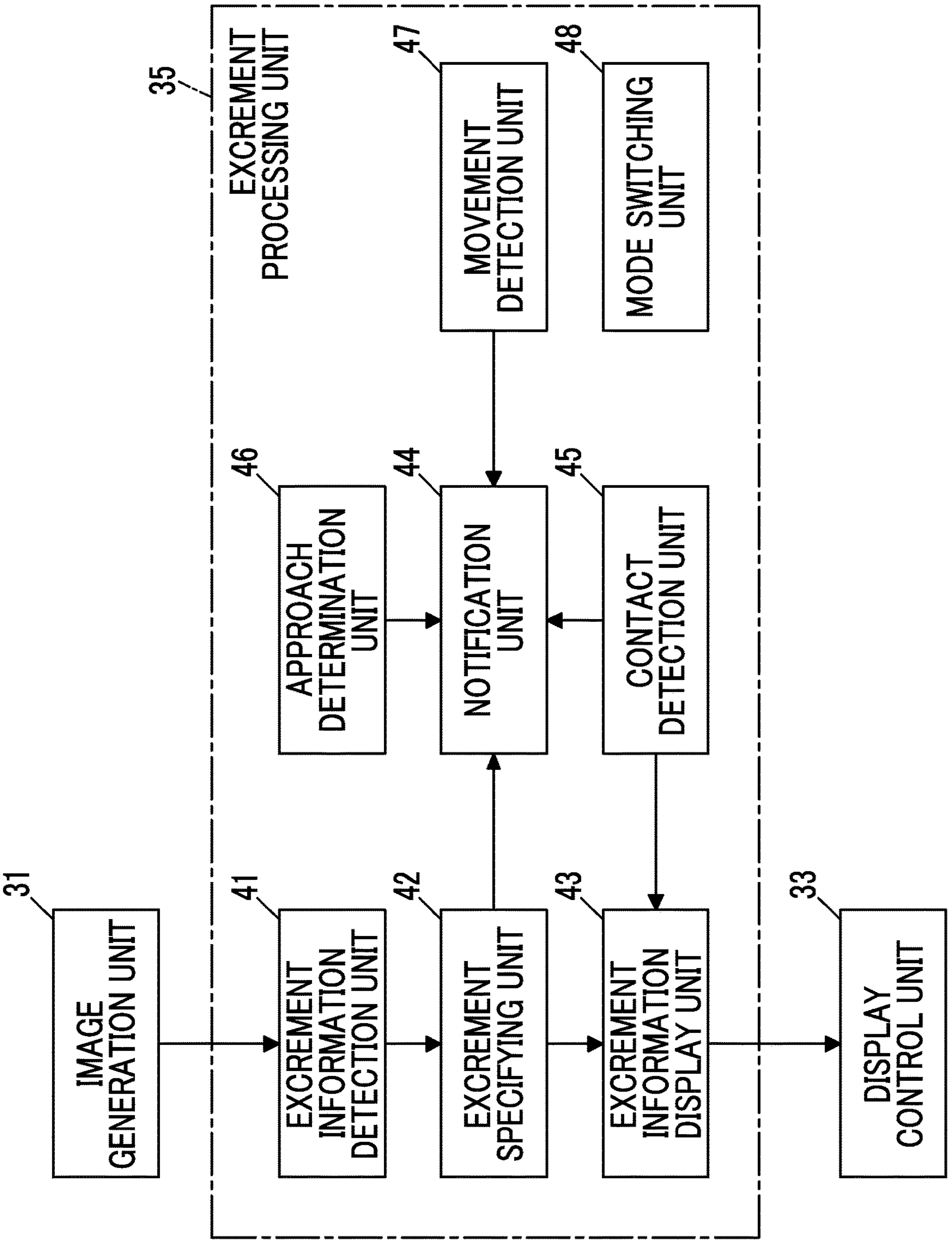
FIG. 4 is a block diagram of an embodiment illustrating a configuration of an excrement processing unit.

Under the control of the apparatus control unit 36, the excrement processing unit 35 performs various types of processing related to excrement, including specifying the presence or absence of excrement in the ultrasound image, specifying an excrement property of an excrement region, and the like. As illustrated in FIG. 4, the excrement processing unit 35 includes an excrement information detection unit 41, an excrement specifying unit 42, a contact detection unit 45, a movement detection unit 47, an excrement information display unit 43, an approach determination unit 46, a notification unit 44, and a mode switching unit 48.

The excrement information detection unit 41 is connected to the image generation unit 31. The excrement specifying unit 42 and the excrement information display unit 43 are sequentially connected to the excrement information detection unit 41, and the display control unit 33 is connected to the excrement information display unit 43. Further, the excrement information display unit 43 is connected to the contact detection unit 45. The notification unit 44 is connected to each of the excrement specifying unit 42, the contact detection unit 45, the approach determination unit 46, and the movement detection unit 47. Although not illustrated, each unit of the excrement processing unit 35 is connected to the mode switching unit 48.

The excrement information detection unit 41 detects various types of information related to excrements from the ultrasound image by analyzing the ultrasound image. For example, the excrement information detection unit 41 detects an excrement region, which is a region where excrement is likely to be present, from the ultrasound image. The excrement information detection unit 41 detects excrement property information, which is information related to an excrement property of the excrement region, from the ultrasound image, in addition to detection of the excrement region.

A detection method of the excrement region is not particularly limited. For example, the excrement information detection unit 41 can detect an excrement region from an ultrasound image by using at least one of template matching, machine learning using image feature amounts, or a deep learning model.

In a case of detecting an excrement region from an ultrasound image by using template matching, the excrement information detection unit 41 prepares a plurality of templates having different sizes, shapes, textures, and the like in a region of interest, and performs raster scanning of the ultrasound image by using each of the plurality of templates. Thereby, a region of which a correlation value with the template is equal to or higher than a predetermined threshold value is detected as an excrement region.

In a case of detecting an excrement region from an ultrasound image by using machine learning using image feature amounts, the excrement information detection unit 41 prepares a plurality of training images including an anatomical structure and an excrement region, converts a region of interest into a feature amount vector (image quantization), and performs machine learning using a machine learning algorithm such as adaptive boosting (Adaboost) or support vector machine (SVM). Thereby, an excrement region is detected from the ultrasound image.

In a case of detecting an excrement region from an ultrasound image by using a deep learning model, the excrement information detection unit 41 prepares a large number of training images including an anatomical structure and an excrement region, creates a deep learning model obtained by learning, for the large number of training images, a relationship between the training image and the excrement region in the training image by using the large number of the training images, and detects an excrement region from the ultrasound image by using the deep learning model.

The excrement specifying unit 42 specifies the presence or absence of excrement, in other words, whether or not the excrement region is a region in which excrement is actually present, based on a detection result of the excrement region. The excrement specifying unit 42 specifies an excrement property of the excrement region based on the excrement property information, in addition to specifying the presence or absence of excrement.

A method of specifying the presence or absence of excrement is not particularly limited. In a case where the excrement specifying unit 42 specifies the presence or absence of excrement but does not specify an excrement property, the excrement specifying unit 42 can specify the presence or absence of excrement based on a detection result of the excrement region in the ultrasound images of the plurality of frames. In this case, the excrement specifying unit 42 specifies that excrement is present, for example, in a case where the excrement regions are detected from the ultrasound images of the frames of a predetermined number or more among the ultrasound images of the plurality of continuous frames. The excrement specifying unit 42 specifies that excrement is present, for example, in a case where the excrement regions are detected from the ultrasound images of eight or more frames among the ultrasound images of continuous 10 frames. Alternatively, the excrement specifying unit 42 may specify that excrement is present only in a case where the excrement regions are detected in all the ultrasound images of 10 frames among the ultrasound images of continuous 10 frames.

In this case, desirably, the excrement specifying unit 42 performs identity determination to determine whether or not the excrement regions in the ultrasound images of the adjacent frames are the identical excrement region, and counts the number of frames of the ultrasound images in which the identical excrement region is detected, as the predetermined number of frames. That is, the excrement specifying unit 42 counts the number of frames only in a case where the excrement regions detected from the ultrasound images of the adjacent frames are the same. Thereby, it is possible to specify that the excrement region which is stably detected at the same position of the ultrasound images of the adjacent frames is a region where excrement is present.

A method of performing identity determination is not particularly limited. For example, the excrement specifying unit 42 can determine whether or not the excrement regions are the same by obtaining an evaluation index based on an intersection over union (IoU) of the excrement regions in the ultrasound images of the adjacent frames, that is, a degree of superimposition of the excrement regions in the ultrasound images of the adjacent frames, and comparing the evaluation index with a threshold value. The excrement specifying unit 42 determines that the excrement regions are the same, for example, in a case where the evaluation index is equal to or higher than the threshold value.

In a case where a plurality of excrement regions are detected in the ultrasound image of one frame, the excrement specifying unit 42 specifies that excrement is present for each excrement region in a case where the excrement regions are detected from the ultrasound images of the frames of a predetermined number or more among the ultrasound images of the plurality of continuous frames. Even in this case, desirably, the excrement specifying unit 42 performs identity determination of the excrement regions in the ultrasound images of the adjacent frames, for each excrement region.

Alternatively, the excrement specifying unit 42 may specify whether or not excrement is present based on a detection result of the excrement region in the ultrasound image of only one frame. In this case, the excrement specifying unit 42 specifies that excrement is present, for example, in a case where an excrement region is detected from the ultrasound image of one frame. That is, the excrement specifying unit 42 specifies that excrement is present in a case where an excrement region is detected even in the ultrasound image of one frame.

When specifying the presence or absence of excrement for each ultrasound image of one frame, in a case where a region where excrement is not actually present is erroneously detected as an excrement region, there is a possibility that it is specified that excrement is present. On the other hand, as described above, by specifying the presence or absence of excrement based on a detection result of the excrement region in the ultrasound images of the plurality of frames, erroneous detection of the excrement region can be significantly reduced, and thus this is more desirable.

In a case of specifying the presence or absence of excrement and specifying an excrement property, for example, the excrement specifying unit 42 can be specify that excrement is present in a case where excrement regions are detected from the ultrasound images of the frames of a predetermined first number or more among the ultrasound images of the plurality of continuous frames and excrement properties of the excrement regions, which are detected from the ultrasound images of the frames of a predetermined second number or more among the ultrasound images of the frames of the predetermined first number or more, are the same.

Even in this case, desirably, the excrement specifying unit 42 performs identity determination of the excrement regions, and counts the number of the frames of the ultrasound images in which the identical excrement region is detected, as the predetermined first frame number and the predetermined second frame number described above.

Similarly, in a case where an excrement region is detected from the ultrasound image of one frame and an excrement property of the excrement region detected from the ultrasound image of one frame is specified, the excrement specifying unit 42 may specify that excrement is present.

Further, the excrement specifying unit 42 can specify the presence or absence of excrement based on a detection result of the excrement region detected by the deep learning model.

In this case, the excrement information detection unit 41 may detect only an excrement region from an ultrasound image by using the deep learning model, or detect an excrement region and a probability that the excrement region is a region of excrement.

In a case of detecting only an excrement region, the excrement information detection unit 41 detects the excrement region as a rectangular region, for example, by using the deep learning model.

In addition, the excrement specifying unit 42 specifies that excrement is present in a case where an excrement region is detected, and specifies that excrement is not present in a case where an excrement region is not detected.

In a case of detecting an excrement region and a probability that the excrement region is a region of excrement, the excrement information detection unit 41 detects an excrement region as a rectangular region for each frame of the ultrasound images by using, for example, the deep learning model, and detects a position of the excrement region and a probability that the excrement region is a region of excrement.

In addition, the excrement specifying unit 42 specifies the presence or absence of excrement by comparing a statistic value of the probabilities of the ultrasound images of the plurality of frames, for example, an average value, a weighted average value, a median value, or the like with a threshold value. The excrement specifying unit 42 specifies that excrement is present, for example, in a case where a statistic value of the probabilities that the excrement region is a region of excrement is equal to or higher than a threshold value.

Alternatively, the excrement information detection unit 41 may detect a probability that a pixel is a pixel of excrement for each pixel of the ultrasound image by using the deep learning model. In this case, the excrement information detection unit 41 detects a probability that a pixel is a pixel of excrement for each frame of the ultrasound images and for each pixel of the ultrasound image, by using the deep learning model, and determines whether or not a pixel is a pixel of excrement by comparing a probability that a pixel is a pixel of excrement with a first threshold value. The excrement information detection unit 41 determines that a pixel is a pixel of excrement, for example, in a case where the probability is equal to or higher than the first threshold value. In addition, the excrement information detection unit 41 detects, as an excrement region, a collection (cluster) of a plurality of pixels that are determined as pixels of excrement.

In addition, the excrement specifying unit 42 obtains, as an index value, a statistic value of the probabilities of all the pixels in the excrement region of the ultrasound image of one frame, for example, an average value, a weighted average value, or a median value, and specifies the presence or absence of excrement by comparing a statistic value of the index values of the ultrasound images of the plurality of frames, for example, an average value, a weighted average value, or a median value with a second threshold value. The excrement specifying unit 42 specifies that excrement is present in a case where, for example, a statistic value of the index values is equal to or higher than the second threshold value.

As described above, even in a case of specifying the presence or absence of excrement by using the deep learning model, desirably, the excrement specifying unit 42 performs identity determination to detect the identical excrement region.

A method of specifying an excrement property is not particularly limited. For example, the excrement specifying unit 42 can specify an excrement property, for example, based on a brightness value of the excrement region or based on excrement property information detected by a deep learning model.

In a case of specifying an excrement property based on a brightness value of an excrement region, for example, the excrement information detection unit 41 detects an excrement region from the ultrasound image, and detects a statistic value of brightness in the excrement region, for example, an average value, a weighted average value, a median value, or the like for each frame of the ultrasound images. In this case, the excrement specifying unit 42 obtains, for each frame of the ultrasound images, a first comparison result by comparing the statistic value of the brightness in the excrement region with a third threshold value, and specifies an excrement property based on the first comparison result in the ultrasound images of one frame or a plurality of frames. For example, the excrement specifying unit 42 specifies that the excrement is hard in a case where the statistic value of the brightness is equal to or higher than a fifth threshold value, specifies that the excrement is normal in a case where the statistic value of the brightness is equal to or higher than a sixth threshold value lower than the fifth threshold value and is lower than the fifth threshold value, and specifies that the excrement is soft in a case where the statistic value of the brightness is lower than the sixth threshold value.

Alternatively, the excrement information detection unit 41 may detect an excrement region from the ultrasound image for each frame of the ultrasound images, and detect a brightness ratio between a statistic value of brightness in the excrement region and a statistic value of brightness in a predetermined region around the excrement region. The excrement specifying unit 42 may obtain a second comparison result for each frame of the ultrasound images by comparing the brightness ratio and a fourth threshold value, and specify an excrement property based on the second comparison result in the ultrasound images of one frame or a plurality of frames. Similarly, the excrement specifying unit 42 specifies that the excrement is hard in a case where the brightness ratio is equal to or higher than a fifth threshold value, specifies that the excrement is normal in a case where the brightness ratio is equal to or higher than a sixth threshold value lower than the fifth threshold value and is lower than the fifth threshold value, and specifies that the excrement is soft in a case where the brightness ratio is lower than the sixth threshold value.

In a case of specifying the excrement property based on the brightness value of the excrement region, there may be cases where the excrement region is detected but the excrement property is specified as being unknown.

In a case of specifying an excrement property based on the excrement property information detected by the deep learning model, the excrement information detection unit 41 simultaneously detects an excrement region and the excrement property information by using, for example, the deep learning model.

In addition, the excrement specifying unit 42 specifies the presence or absence of excrement based on the excrement region detected by the deep learning model, and specifies an excrement property based on the excrement property information detected by the deep learning model.

In this case, the excrement information detection unit 41 may detect, as the excrement property information, a probability that the excrement region is included in each class of excrement properties, for example, a probability that the excrement is hard, soft, normal, or background, or may detect a probability that a pixel is included in each class of excrement properties for each pixel of the ultrasound image.

In a case of detecting a probability that the excrement region is included in each class of the excrement properties, for example, the excrement information detection unit 41 detects an excrement region as a rectangular region by using the deep learning model, and detects a probability that the excrement region is included in each class of the excrement properties.

In addition, the excrement specifying unit 42 specifies a class having a highest probability among the classes of the excrement properties, as the excrement property of the excrement region.

In a case of detecting, for each pixel of the ultrasound image, a probability that the pixel is included in each class of the excrement properties, for example, the excrement information detection unit 41 detects, for each pixel of the ultrasound image, a probability that the pixel is included in each class of the excrement properties by using a deep learning model, and determines a class having a highest probability among the classes of the excrement properties, as a class of the pixel. In addition, the excrement information detection unit 41 detects, as an excrement region, a collection (cluster) of a plurality of pixels determined as pixels of excrement based on the classes of the pixels.

In this case, a plurality of pixels having different classes may be mixed in one excrement region. Accordingly, the excrement specifying unit 42 obtains a total area of the classes for each class of the excrement properties, and specifies a class having a largest total area, as the excrement property of the excrement region.

The contact detection unit 45 detects whether or not the ultrasound probe 1 is brought into contact with the examination area of the subject during performing scanning.

The contact detection unit 45 is not particularly limited. For example, the contact detection unit 45 can detect whether or not the ultrasound probe 1 is brought into contact with the examination area of the subject based on at least one of an analysis result of the ultrasound image or a pressure detection result by the pressure sensor 13.

The movement detection unit 47 detects the presence or absence of a movement of the ultrasound probe 1 during performing scanning. For example, the movement detection unit 47 detects the presence or absence of a movement of the ultrasound probe 1 for each frame of the ultrasound images after scanning is started.

The movement detection unit 47 is not particularly limited. For example, the movement detection unit 47 can detect the presence or absence of a movement of the ultrasound probe 1 based on at least one of an image analysis result of the ultrasound image, a movement detection result obtained by the motion sensor 12 provided in the ultrasound probe 1, or a pressure detection result by the pressure sensor 13 provided in the ultrasound probe 1.

In a case where the presence or absence of motion of the ultrasound probe 1 is detected based on the pressure detection result by the pressure sensor 13, the pressure detection result by the pressure sensor 13 changes only in a case where the ultrasound probe 1 is moved. Therefore, by comparing a change amount in the pressure detected by the pressure sensor 13 with a threshold value, it is possible to detect the presence or absence of a movement of the ultrasound probe 1. For example, in a case where the change amount is equal to or larger than the threshold value, the presence of a movement of the ultrasound probe 1 is detected.

The excrement information display unit 43 displays various types of information related to the excrement on the monitor 34 under a control of the display control unit 33. For example, in a case where it is specified that excrement is present, the excrement information display unit 43 highlight-displays an excrement region in the ultrasound image displayed on the monitor 34.

A method of highlight-displaying the excrement region is not particularly limited. For example, a contour line may be created by detecting a contour of the excrement region, and the contour line may be displayed by being superimposed on the contour of the excrement region. Alternatively, a surrounding line of any shape such as a circle or a rectangle is created, and a region larger than the excrement region and including the excrement region may be surrounded by the surrounding line. In this case, the contour line or the surrounding line may be displayed with a predetermined display color, may be displayed in a predetermined line type, or may be displayed in a predetermined thickness. In addition, a mask obtained by coloring and filling the inside of the excrement region with a predetermined display color is created, and the mask may be displayed by superimposing the mask on the excrement region.

The approach determination unit 46 determines an approach of the ultrasound probe 1 during performing scanning. In other words, the approach determination unit 46 determines the current approach of the ultrasound probe 1 during scanning.

The approach of the ultrasound probe 1 includes, for example, a rectal longitudinal section approach in which abdomen of the subject is scanned from the front side of the subject with the ultrasound probe 1 in vertical orientation, a rectal transverse section approach in which abdomen of the subject is scanned from the front side of the subject with the ultrasound probe 1 in transverse orientation, and an intergluteal cleft approach in which abdomen of the subject is scanned from the intergluteal cleft on the back side of the subject using the ultrasound probe.

The approach determination method is not particularly limited. For example, for each approach, it is possible to determine an approach from ultrasound images using a deep learning model obtained by learning a relationship between a training image and an approach corresponding to the training image using a large number of training images.

The notification unit 44 notifies the user of various messages. For example, in a case where it is not specified that excrement is present within a predetermined period, the notification unit 44 notifies the user of a message suggesting a change of the approach of the ultrasound probe 1 during performing scanning.

The predetermined period is not particularly limited, and is a period during which it is assumed that the presence or absence of excrement can be specified based on the detection result of the excrement region at the examination area of the subject. A length of the predetermined period is not particularly limited, and may be, for example, a period during which examination related to the presence or absence of excrement is performed on the examination area of the subject by using the ultrasound probe, such as a period during which scanning of the examination area of the subject is performed, a period during which examination of the examination area of the subject is performed, a period during which the ultrasound probe is brought into contact with the examination area of the subject, or a period from only a time at which a movement of the ultrasound probe is detected. In addition, the predetermined period may be a fixed period, for example, 5 seconds, 10 seconds, or 20 seconds. Alternatively, as the predetermined period, a longest time during which scanning of the examination area of the subject is performed, for example, 20 seconds, 30 seconds, 1 minute, or the like may be determined.

In addition, measurement of the predetermined period is not particularly limited, and may be started, for example, immediately after scanning is started. Alternatively, measurement of the predetermined period may be started from immediately after examination of the examination area of the subject is started, in other words, immediately after a function of examining constipation (presence or absence of excrement) is activated in the ultrasound diagnostic apparatus. In addition, measurement of the predetermined period may be started immediately after the contact detection unit 45 detects that the ultrasound probe 1 is brought into contact with the examination area of the subject. Further, only a time during which a movement of the ultrasound probe 1 is detected by the movement detection unit 47 may be measured as the predetermined period.

A notification method of a message is not particularly limited. For example, under a control of the display control unit 33, a message may be displayed on the monitor 34, a voice for reading the message may be output from a speaker (not illustrated), or both the methods may be simultaneously performed.

The ultrasound diagnostic apparatus has at least two operation modes among a first operation mode in which both the presence or absence of excrement and an excrement property are not specified, a second operation mode in which the presence or absence of the excrement is specified but an excrement property is not specified, and a third operation mode in which both the presence or absence of excrement and an excrement property are specified.

The mode switching unit 48 switches the operation mode to one operation mode of at least two operation modes described above in response to an instruction input from the user by using a GUI, voice recognition, or the like.

The image generation unit 31, the excrement processing unit 35, the display control unit 33, and the apparatus control unit 36 are configured by a processor 39.

Figure 5:
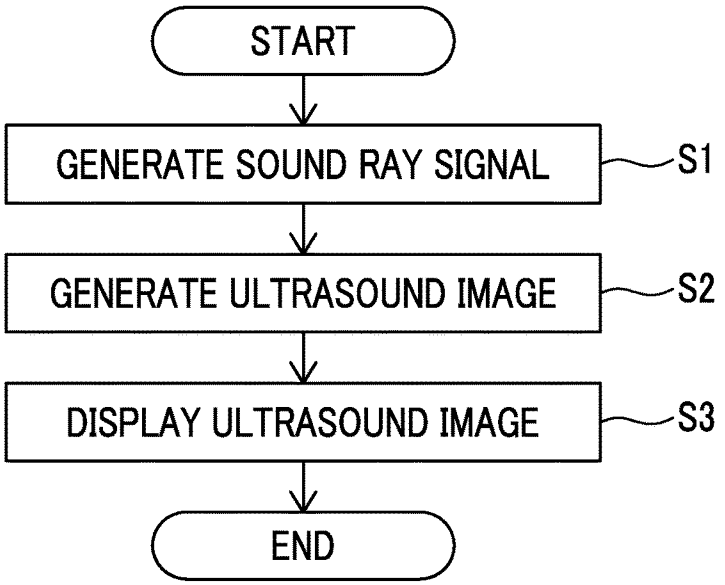
FIG. 5 is a flowchart of an embodiment illustrating an operation of the ultrasound diagnostic apparatus in a first operation mode.

Next, an operation of the ultrasound diagnostic apparatus in the first operation mode will be described with reference to a flowchart of FIG. 5.

In this case, first, in a state where the ultrasound probe 1 is in contact with the examination area of the subject, under the control of the apparatus control unit 36, transmission of the ultrasound waves is started by the transmission/reception circuit 14, and the sound ray signal is generated (step S1).

That is, the ultrasound beams are transmitted to the examination area of the subject from the plurality of transducers of the transducer array 11 in accordance with the drive signal from the pulser 51.

The ultrasound echoes from the examination area based on the ultrasound beams transmitted from the pulser 51 are received by each transducer of the transducer array 11, and the reception signal as an analog signal is output from each transducer of the transducer array 11 that receives the ultrasound echoes.

The reception signal output from each transducer of the transducer array 11 is amplified by the amplification unit 52, and is subjected to AD conversion by the AD conversion unit 53. Thereby, the reception data is acquired.

By performing the reception focusing processing on the reception data by the beam former 54, the sound ray signal is generated.

Next, under the control of the apparatus control unit 36, the ultrasound image (ultrasound image signal) of the examination area of the subject is generated by the image generation unit 31 based on the sound ray signal generated by the beam former 54 of the transmission/reception circuit 14 (step S2).

That is, the sound ray signal generated by the beam former 54 is subjected to various kinds of signal processing by the signal processing unit 16, and the image information data representing tomographic image information related to tissues inside the subject is generated. The image information data generated by the signal processing unit 16 is raster-converted by the DSC 18, and is further subjected to various kinds of image processing by the image processing unit 17. Thereby, the ultrasound image (ultrasound image signal) is generated. The ultrasound image generated by the image processing unit 17 is stored in the image memory 32.

Next, under the control of the apparatus control unit 36, predetermined processing is performed on the ultrasound image generated by the image processing unit 17 or the ultrasound image stored in the image memory 32 by the display control unit 33, and the processed ultrasound image is displayed on the monitor 34 (step S3).

Figure 6:
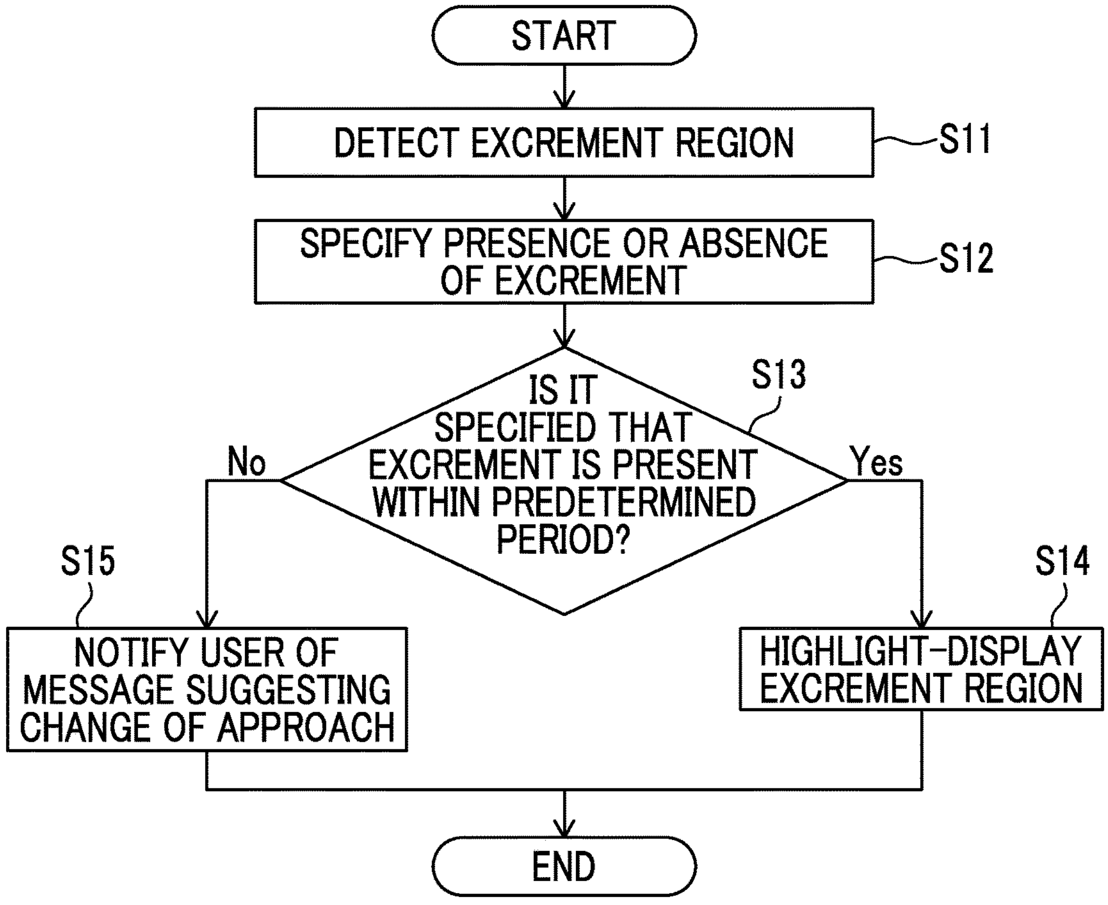
FIG. 6 is a flowchart of an embodiment illustrating an operation of the ultrasound diagnostic apparatus in a second operation mode.

Next, an operation of the ultrasound diagnostic apparatus in the second operation mode will be described with reference to a flowchart illustrated in FIG. 6.

In this case, the operation from generation of the ultrasound image to display of the ultrasound image on the monitor 34 is the same as the operation in the first operation mode. In addition, the excrement information detection unit 41 analyzes the ultrasound image, and detects an excrement region from the ultrasound image (step S11).

Subsequently, the excrement specifying unit 42 specifies the presence or absence of excrement based on a detection result of the excrement region (step S12).

As a result, in a case where it is specified that excrement is present (Yes in step S13), under the control of the display control unit 33, the excrement information display unit 43 highlight-displays the excrement region in the ultrasound image displayed on the monitor 34 (step S14).

Figure 9:
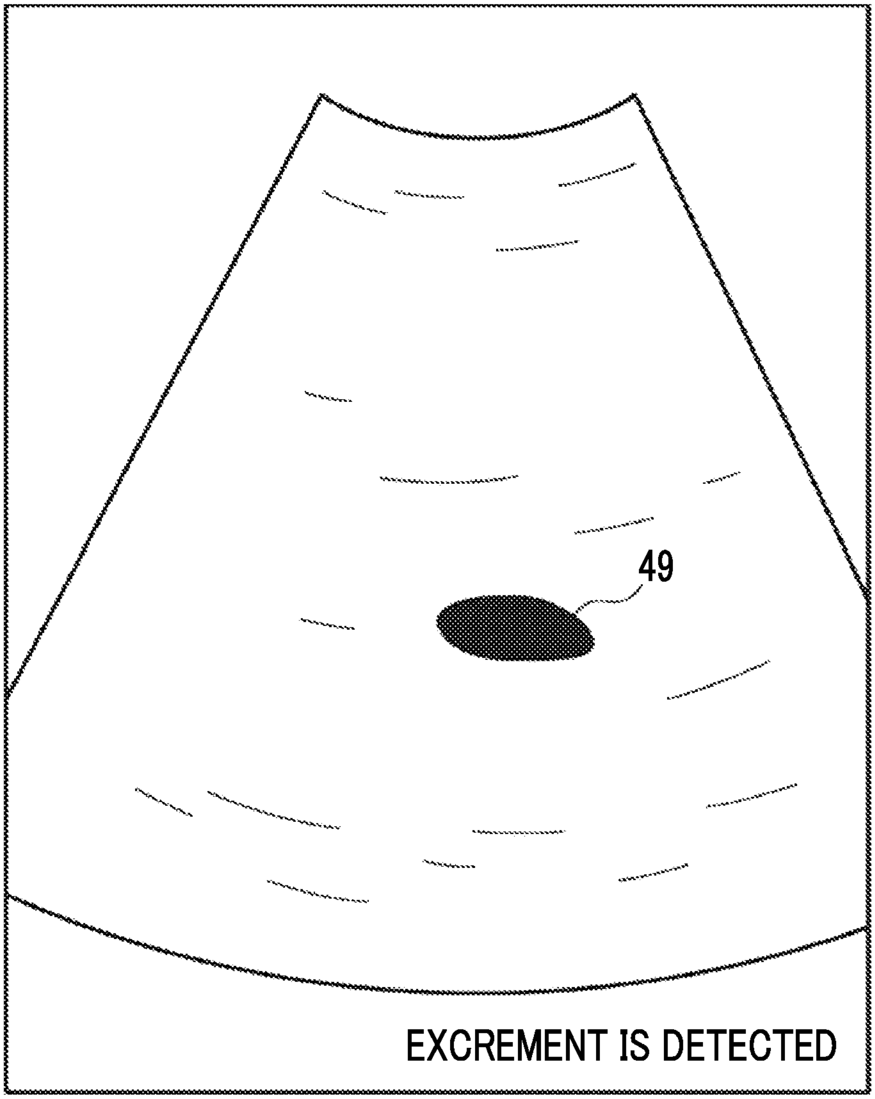
FIG. 9 is a conceptual diagram of an embodiment illustrating a display screen of a monitor of the ultrasound diagnostic apparatus in a case of notifying a user of a message representing that excrement is present.

The excrement information display unit 43 creates, for example, a mask 49 for highlight-displaying the excrement region, and displays the mask 49 by superimposing the mask 49 on the excrement region of the ultrasound image displayed on the monitor 34 as illustrated in FIG. 9. In this case, the notification unit 44 may notify the user of a message representing that excrement is present. For example, as illustrated in FIG. 9, a message such as "excrement is detected" may be displayed on the monitor 34.

Figure 10:
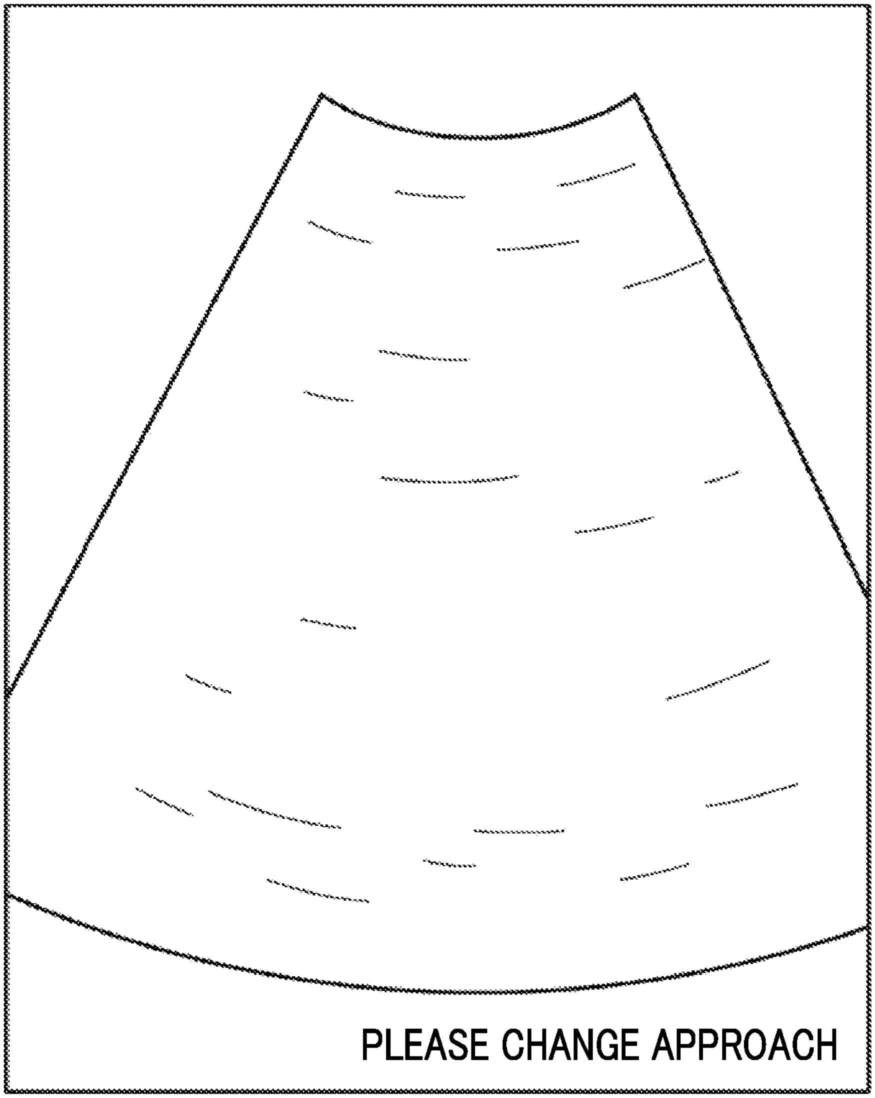
FIG. 10 is a conceptual diagram of an embodiment illustrating a display screen of a monitor of the ultrasound diagnostic apparatus in a case of notifying a user of a message suggesting a change of an approach of an ultrasound probe.

On the other hand, in a case where it is not specified that excrement is present within a predetermined period (No in step S13), the notification unit 44 notifies the user of a message suggesting a change of the approach of the ultrasound probe 1 during performing scanning (step S15). For example, as illustrated in FIG. 10, a message such as "please change approach" is displayed on the monitor 34.

The user changes the approach according to the message, and performs scanning again.

As described above, in a case where it is specified that excrement is present, in the ultrasound diagnostic apparatus, the excrement region is highlight-displayed in the ultrasound image displayed on the monitor 34. Therefore, the user can easily recognize the excrement region in the ultrasound image. Further, even in a case where it is not specified that excrement is present within the predetermined period, notification of a message suggesting a change of the approach is performed. Therefore, the user can change the approach according to the message, and thus the presence or absence of excrement can be reliably specified.

Figure 7:
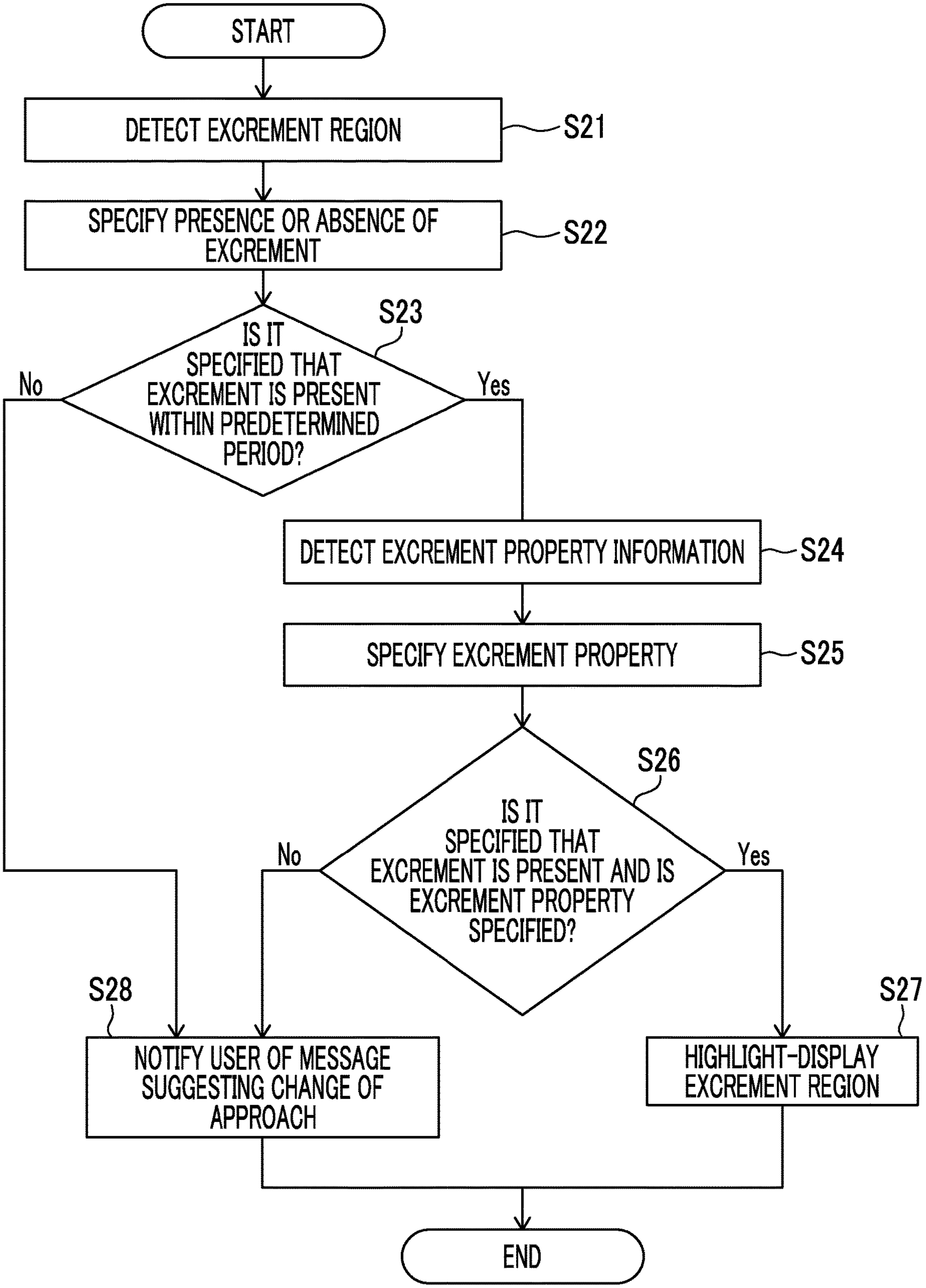
FIG. 7 is a flowchart of an embodiment illustrating an operation of the ultrasound diagnostic apparatus in a third operation mode.

Next, an operation of the ultrasound diagnostic apparatus in the third operation mode will be described. In the third operation mode, the excrement property information can be detected after the excrement region is detected, or the excrement region and the excrement property information can be simultaneously detected. First, a case where the excrement property information is detected after the excrement region is detected in the third operation mode will be described with reference to a flowchart illustrated in FIG. 7.

Even in this case, the operation from generation of the ultrasound image to display of the ultrasound image on the monitor 34 is the same as the operation in the first operation mode. In addition, the excrement information detection unit 41 analyzes the ultrasound image, and detects an excrement region from the ultrasound image (step S21).

Subsequently, the excrement specifying unit 42 specifies the presence or absence of excrement based on a detection result of the excrement region (step S22).

As a result, in a case where it is not specified that excrement is present within the predetermined period (No in step S23), the process proceeds to step S28.

On the other hand, in a case where it is specified that excrement is present (Yes in step S23), the excrement information detection unit 41 further detects excrement property information of the excrement region from the ultrasound image (step S24).

Subsequently, the excrement specifying unit 42 further specifies an excrement property of the excrement region based on the excrement property information (step S25).

As a result, in a case where it is specified that excrement is present and the excrement property is specified (Yes in step S26), the excrement information display unit 43 highlight-displays the excrement region in the ultrasound image displayed on the monitor 34 (step S27). In this case, the notification unit 44 may notify the user of a message representing that excrement is present, may notify the user of a message representing an excrement property, or may notify the user of both a message representing that excrement is present and a message representing an excrement property.

On the other hand, in a case where it is not specified that excrement is present within a predetermined period or in a case where it is specified that excrement is present but an excrement property is not specified (No in step S26), the notification unit 44 notifies the user of a message suggesting a change of the approach (step S28). The user changes the approach according to the message, and performs scanning again.

Figure 8:
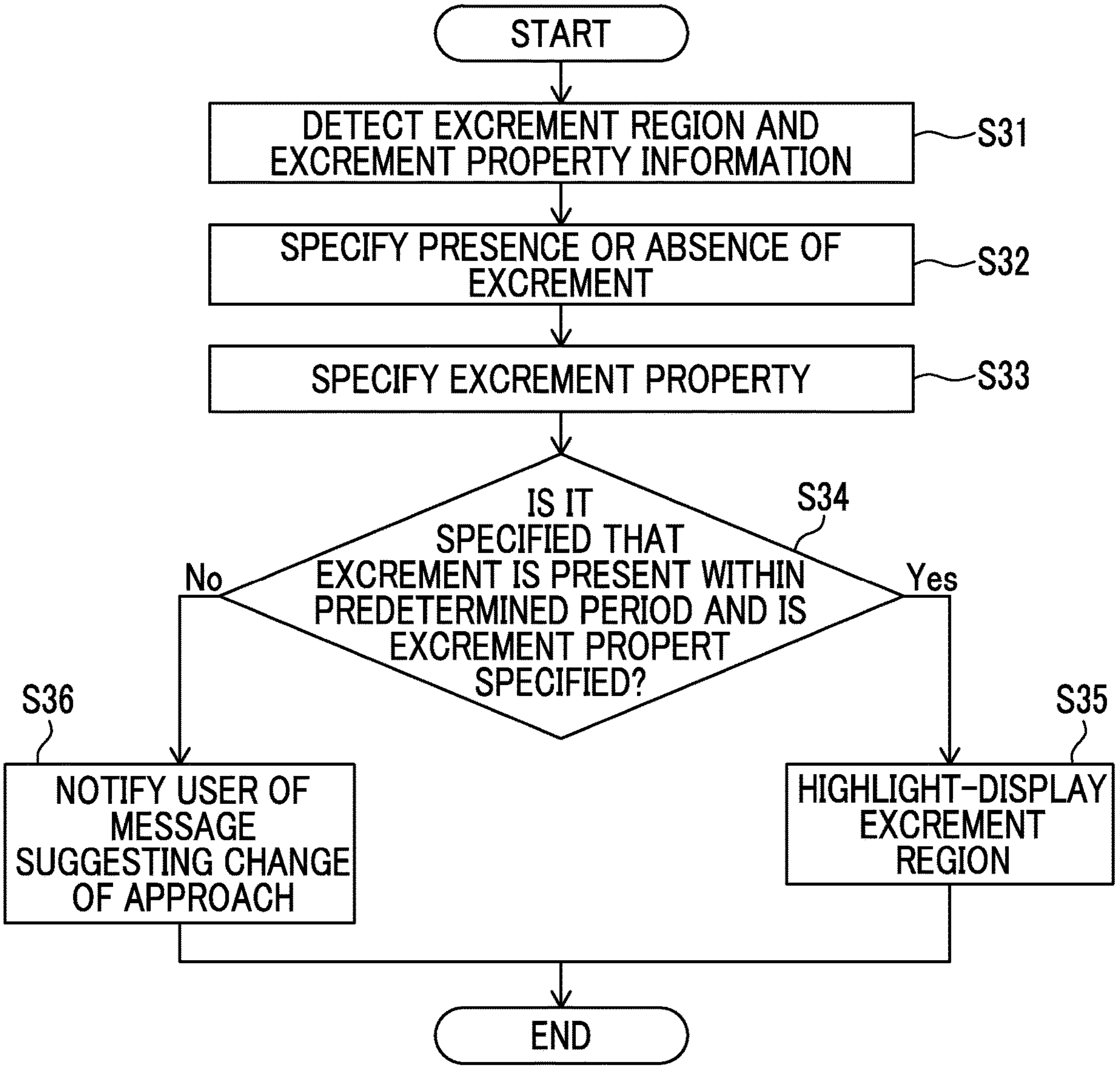
FIG. 8 is a flowchart of another embodiment illustrating an operation of the ultrasound diagnostic apparatus in a third operation mode.

Next, a case where the excrement region and the excrement property information are simultaneously detected in the third operation mode will be described with reference to a flowchart illustrated in FIG. 8.

In this case, the excrement information detection unit 41 simultaneously detects the excrement region and the excrement property information of the excrement region by using, for example, the deep learning model (step S31).

Subsequently, the excrement specifying unit 42 specifies the presence or absence of excrement based on a detection result of the excrement region (step S32), and specifies an excrement property based on the excrement property information (step S33).

The subsequent operations in step S34 to step S36 are the same as the operations in step S26 to step S28 in the case where the excrement property information is detected after the excrement region is detected.

As described above, in a case where it is specified that excrement is present and the excrement property is specified, in the ultrasound diagnostic apparatus, the excrement region is highlight-displayed in the ultrasound image displayed on the monitor 34. Therefore, the user can easily recognize the excrement region in the ultrasound image. Further, even in a case where it is not specified that excrement is present within the predetermined period, or even in a case where it is specified that excrement is present but an excrement property is not specified, notification of a message suggesting a change of the approach is performed. Therefore, the user can change the approach according to the message, and thus the presence or absence of excrement can be reliably specified.

In a case where it is not specified that excrement is present within the predetermined period, the notification unit 44 may suggest a change to an approach different from the current approach.

In this case, the approach determination unit 46 determines the current approach of the ultrasound probe 1 during scanning.

In addition, in a case where it is not specified that excrement is present within the predetermined period, the notification unit 44 selects an approach different from the current approach from among a plurality of preset approaches based on the approach determination result by the approach determination unit 46, and notifies the user of a message suggesting a change to an approach different from the current approach. Further, in a case where it is not specified that excrement is present by all of the plurality of preset approaches, the notification unit 44 may notify the user of a message representing that excrement is not present.

Figure 11:
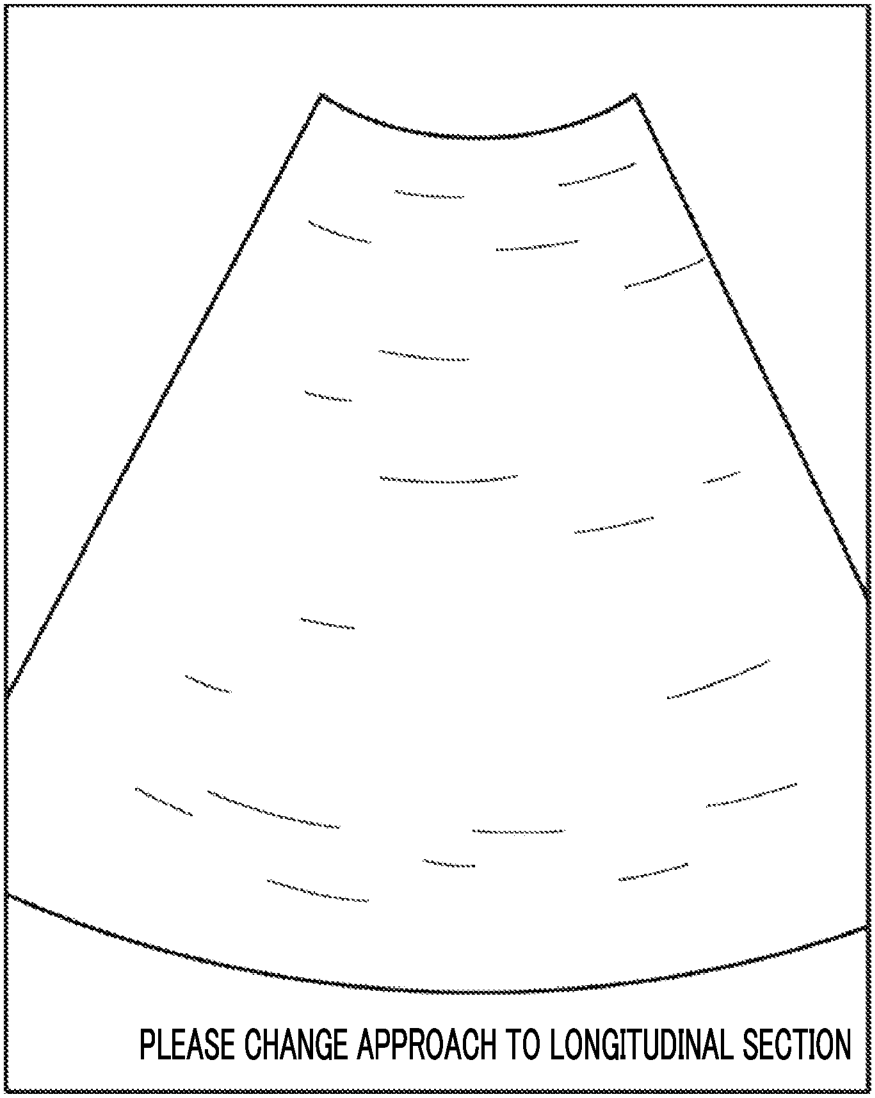
FIG. 11 is a conceptual diagram of another embodiment illustrating a display screen of a monitor of the ultrasound diagnostic apparatus in a case of notifying a user of a message suggesting a change of an approach of an ultrasound probe.

For example, in a case where the approach determination unit 46 determines that the current approach is a rectal transverse section approach, the notification unit 44 selects an approach different from the rectal transverse section approach, for example, a rectal longitudinal section approach, from among the plurality of preset approaches, and notifies the user of a message suggesting a change to the rectal longitudinal section approach. For example, as illustrated in FIG. 11, a message such as "please change to longitudinal section" may be displayed on the monitor 34.

As described above, since constipation diagnosis using an ultrasound image has not yet become fully widespread as a diagnosis method and an examination method, the user may be confused on the approach of the ultrasound probe 1 during performing scanning for constipation diagnosis. On the other hand, as described above, by suggesting a specific approach different from the current approach, the user can change the approach to the suggested approach without hesitation, and thus this is very useful.

A method of selecting an approach different from the current approach from among the plurality of preset approaches is not particularly limited. For example, the selection order can be predetermined, and the approaches can be sequentially selected according to the predetermined selection order.

The present invention is not limited to a stationary ultrasound diagnostic apparatus, and can be similarly applied to a portable ultrasound diagnostic apparatus in which an apparatus main body 3 is realized by a laptop terminal device, and a handheld ultrasound diagnostic apparatus in which an apparatus main body 3 is realized by a handheld terminal device such as a smartphone or a tablet personal computer (PC). In addition, the ultrasound probe 1 and the apparatus main body 3 may be connected in a wired or wireless manner. Further, the entire image generation unit 31 or only the signal processing unit 16 may be provided on the ultrasound probe 1 side, or provided on the apparatus main body 3 side.

In the apparatus of the present invention, as the hardware configurations of the processing units that execute various kinds of processing, such as the transmission/reception circuit 14, the image generation unit 31, the display control unit 33, the excrement processing unit 35, and the apparatus control unit 36, dedicated hardware may be used, or various processors or computers that execute programs may be used.

The various processors include a central processing unit (CPU), which is a general-purpose processor that executes software (program) and functions as the various processing units, a programmable logic device (PLD), which is a processor of which a circuit configuration can be changed after manufacture, such as a field programmable gate array (FPGA), and a dedicated electric circuit, which is a processor having a circuit configuration that is designed for exclusive use in order to execute specific processing, such as an application specific integrated circuit (ASIC).

One processing unit may be configured by using one of the various processors or may be configured by using a combination of two or more processors of the same type or different types, for example, a combination of a plurality of FPGAs or a combination of an FPGA and a CPU. In addition, a plurality of processing units may be configured by using one of various processors, or two or more of the plurality of processing units may be collectively configured by using one processor.

For example, first, as represented by a computer, such as a client and a server, there is a form in which one processor is configured by using a combination of one or more CPUs and software and this processor functions as the plurality of processing units. In addition, as represented by a system on chip (SoC) or the like, there is a form in which a processor that realizes functions of an entire system including a plurality of processing units with one integrated circuit (IC) chip is used.

Further, the hardware configuration of these various processors is, more specifically, an electric circuit (circuitry) in which circuit elements, such as semiconductor elements, are combined.

In addition, the method according to the embodiment of the present invention can be implemented, for example, by a program for causing a computer to execute each of the steps of the method. In addition, a computer-readable recording medium on which the program is recorded can be provided.

Although the present invention is described in detail above, the present invention is not limited to the embodiment described above, and it is needless to say that various improvements or changes may be made without departing from the gist of the present invention.

From the above detailed description of the present invention, the present invention can be implemented as an embodiment described in the following appendix.

APPENDIX

An ultrasound diagnostic apparatus comprising:

an ultrasound probe;

a monitor; and a processor, wherein the processor is configured to:

generate an ultrasound image based on a reception signal obtained by scanning an examination area of a subject with ultrasound beams using the ultrasound probe;

display the ultrasound image on the monitor;

detect an excrement region from the ultrasound image;

specify the presence or absence of excrement based on a detection result of the excrement region;

highlight-display the excrement region in the ultrasound image displayed on the monitor in a case where it is specified that the excrement is present; and notify a user of a message suggesting a change of an approach of the ultrasound probe during performing the scanning in a case where it is not specified that the excrement is present within a predetermined period.

EXPLANATION OF REFERENCES

1: ultrasound probe
3: apparatus main body
11: transducer array
12: motion sensor
13: pressure sensor
14: transmission/reception circuit
16: signal processing unit
17: image processing unit
18: DSC
31: image generation unit
32: image memory
33: display control unit
34: monitor
35: excrement processing unit
36: apparatus control unit
37: input device
39: processor
41: excrement information detection unit
42: excrement specifying unit
43: excrement information display unit
44: notification unit
45: contact detection unit
46: approach determination unit
47: movement detection unit
48: mode switching unit
49: mask
51: pulser
52: amplification unit
53: AD conversion unit
54: beam former

What is claimed is:

1. An ultrasound diagnostic apparatus comprising:

an ultrasound probe;

a monitor; and a processor, wherein the processor is configured to:

sequentially generate a plurality of ultrasound images based on a reception signal obtained by scanning an examination area of a subject with ultrasound beams using the ultrasound probe;

sequentially display each of the plurality of ultrasound images on the monitor;

detect an excrement region, which is a region where excrement is likely to be present, from each of the plurality of ultrasound images;

specify a presence or absence of the excrement by detecting the excrement region from one or more ultrasound images among the plurality of ultrasound images based on a detection result of the excrement region;

highlight-display the excrement region in each of the plurality of ultrasound images sequentially displayed on the monitor in a case where it is specified that the excrement is present; and notify a user of a message suggesting a change of an approach of the ultrasound probe during performing the scanning in a case where it is not specified that the excrement is present within a predetermined period, wherein the processor detects, for each of the plurality of ultrasound images and for each pixel of each of the plurality of ultrasound images, a probability that each pixel is a pixel of the excrement, determines whether or not each pixel is a pixel of the excrement by comparing the probability that each pixel is the pixel of the excrement with a first threshold value, and detects, as the excrement region, a collection of a plurality of pixels that are determined as pixels of the excrement, and the processor obtains, as an index value, a first statistic value of the probability of each pixel in the excrement region of a first ultrasound image among the plurality of ultrasound images, and specifies the presence or absence of the excrement by comparing a second statistic value of index values of each of the plurality of ultrasound images with a second threshold value.

2. The ultrasound diagnostic apparatus according to claim 1, wherein the processor detects the excrement region from each of the plurality of ultrasound images by using at least one of template matching, machine learning using image feature amounts, or a deep learning model.

3. The ultrasound diagnostic apparatus according to claim 1, wherein the processor specifies that the excrement is present in a case where the excrement region is detected from a second ultrasound image among the plurality of ultrasound images.

4. The ultrasound diagnostic apparatus according to claim 1, wherein the processor specifies that the excrement is present in a case where the excrement region is detected from each of a predetermined number or more of the ultrasound images among two or more continuous ultrasound images among the plurality of ultrasound images.

5. The ultrasound diagnostic apparatus according to claim 4, wherein the processor performs identity determination to determine whether or not the excrement region in each of adjacent ultrasound images among the plurality of ultrasound images is an identical excrement region, and counts the number of ultrasound images in which the identical excrement region is detected, as the predetermined number.

6. The ultrasound diagnostic apparatus according to claim 5, wherein the processor performs the identity determination for each excrement region of a plurality of excrement regions in a case where the plurality of excrement regions are detected in a third ultrasound image among the plurality of ultrasound images.

7. The ultrasound diagnostic apparatus according to claim 1, wherein measurement of the predetermined period is started immediately after the scanning is started.

8. The ultrasound diagnostic apparatus according to claim 1, wherein measurement of the predetermined period is started immediately after examination of the examination area of the subject is started.

9. The ultrasound diagnostic apparatus according to claim 1, wherein the processor is further configured to detect whether or not the ultrasound probe is brought into contact with the examination area of the subject, wherein measurement of the predetermined period is started immediately after contact of the ultrasound probe with the examination area of the subject is detected.

10. The ultrasound diagnostic apparatus according to claim 1, wherein the processor is further configured to detect a presence or absence of a movement of the ultrasound probe, wherein only a time during which the movement of the ultrasound probe is detected is measured as the predetermined period.

11. The ultrasound diagnostic apparatus according to claim 10, wherein the processor detects the presence or absence of the movement of the ultrasound probe based on at least one of an image analysis result of the plurality of ultrasound images, a movement detection result obtained by a motion sensor provided in the ultrasound probe, or a pressure detection result by a pressure sensor provided in the ultrasound probe.

12. The ultrasound diagnostic apparatus according to claim 1, wherein the processor notifies a user of a message representing that the excrement is present in a case where it is specified that the excrement is present.

13. The ultrasound diagnostic apparatus according to claim 1, wherein the processor is further configured to determine the approach, wherein the processor selects a second approach different from the approach with which scanning is being performed from among a plurality of preset approaches in a case where it is not specified that the excrement is present within the predetermined period, and notifies a user of a message suggesting a change to the second approach different from the approach with which scanning is being performed.

14. The ultrasound diagnostic apparatus according to claim 13, wherein the processor notifies a user of a second message representing that the excrement is not present in a case where it is not specified that the excrement is present by all of the plurality of preset approaches.

15. The ultrasound diagnostic apparatus according to claim 1, wherein the processor further detects excrement property information of the excrement region from each of the plurality of ultrasound images, the processor further specifies an excrement property of the excrement region based on the excrement property information, the processor highlight-displays the excrement region in each of the plurality of ultrasound images sequentially displayed on the monitor in a case where it is specified that the excrement is present and the excrement property is specified, and the processor notifies a user of a message suggesting a change of the approach in a case where it is not specified that the excrement is present within the predetermined period or in a case where it is specified that the excrement is present but the excrement property is not specified.

16. The ultrasound diagnostic apparatus according to claim 15, wherein the processor detects, for each of the plurality of ultrasound images, a statistic value of brightness in the excrement region, and the processor obtains, for each of the plurality of ultrasound images, a first comparison result by comparing the statistic value of brightness in the excrement region with a third threshold value, and specifies the excrement property based on one first comparison result in the first ultrasound image or a plurality of first comparison results in the plurality of ultrasound images, or the processor detects, for each of the plurality of ultrasound images, a brightness ratio between the statistic value of brightness in the excrement region and a statistic value of brightness in a predetermined region around the excrement region, and the processor obtains, for each of the plurality of ultrasound images, a second comparison result by comparing the brightness ratio with a fourth threshold value, and specifies the excrement property based on one second comparison result in the first ultrasound image or a plurality of second comparison results in the plurality of ultrasound images.

17. The ultrasound diagnostic apparatus according to claim 15, wherein the processor detects the excrement region and a probability that the excrement region is included in each of classes of excrement properties, and the processor specifies a class having a highest probability among the classes of the excrement properties, as the excrement property of the excrement region.

18. The ultrasound diagnostic apparatus according to claim 15, wherein the processor detects, for each pixel of each of the plurality of ultrasound images, a probability that each pixel is included in each of classes of the excrement properties, determines, among the classes of the excrement properties, a class having a highest probability as a class of each pixel, and detects, as the excrement region, a collection of the plurality of pixels that are determined as pixels of the excrement based on the class of each pixel, and the processor obtains a total area of the classes for each of the classes of the excrement properties, and specifies a class having a largest total area, as the excrement property of the excrement region.

19. The ultrasound diagnostic apparatus according to claim 15, wherein the processor specifies that the excrement is present in a case where the excrement region is detected from a second ultrasound image among the plurality of ultrasound images and the excrement property of the excrement region detected from the the first ultrasound image is specified.

20. The ultrasound diagnostic apparatus according to claim 15, wherein the processor specifies that the excrement is present in a case where the excrement region is detected from each of a predetermined first number or more of the ultrasound images among a plurality of two or more continuous ultrasound images among the plurality of ultrasound images and the excrement property of the excrement region, which are detected from each of ultrasound images of a predetermined second number or more among the ultrasound images of the predetermined first number or more, are the same.

21. The ultrasound diagnostic apparatus according to claim 20, wherein the processor performs identity determination to determine whether or not the excrement region in each of adjacent ultrasound images among the plurality of ultrasound images is the identical excrement region, and counts the number of the ultrasound images in which the identical excrement region is detected, as the predetermined first number and the predetermined second number.

22. The ultrasound diagnostic apparatus according to claim 15, wherein the ultrasound diagnostic apparatus has at least two operation modes among a first operation mode in which both the presence or absence of the excrement and the excrement property are not specified, a second operation mode in which the presence or absence of the excrement is specified but the excrement property is not specified, and a third operation mode in which both the presence or absence of the excrement and the excrement property are specified, and the processor is further configured to switch an operation mode to one operation mode among the at least two operation modes according to an instruction from a user.

23. A control method for an ultrasound diagnostic apparatus, the method comprising:

sequentially generating, via a processor, a plurality of ultrasound images based on a reception signal obtained by scanning an examination area of a subject with ultrasound beams using an ultrasound probe;

sequentially displaying, via the processor, each of the plurality of ultrasound images on a monitor;

detecting, via the processor, an excrement region, which is a region where excrement is likely to be present, from each of the plurality of ultrasound images;

specifying, via the processor, a presence or absence of the excrement by detecting the excrement region from one or more ultrasound images among the plurality of ultrasound images based on a detection result of the excrement region;

highlight-displaying, via the processor, the excrement region in each of the plurality of ultrasound images sequentially displayed on the monitor in a case where it is specified that the excrement is present; and notifying a user of, via the processor, a message suggesting a change of an approach of the ultrasound probe during performing the scanning in a case where it is not specified that the excrement is present within a predetermined period, wherein the processor detects, for each of the plurality of ultrasound images and for each pixel of each of the plurality of ultrasound images, a probability that each pixel is a pixel of the excrement, determines whether or not each pixel is a pixel of the excrement by comparing the probability that each pixel is the pixel of the excrement with a first threshold value, and detects, as the excrement region, a collection of a plurality of pixels that are determined as pixels of the excrement, and the processor obtains, as an index value, a first statistic value of the probability of each pixel in the excrement region of a first ultrasound image among the plurality of ultrasound images, and specifies the presence or absence of the excrement by comparing a second statistic value of index values of each of the plurality of ultrasound images with a second threshold value.

24. An ultrasound diagnostic apparatus comprising:

an ultrasound probe;

a monitor; and a processor, wherein the processor is configured to:

sequentially generate a plurality of ultrasound images based on a reception signal obtained by scanning an examination area of a subject with ultrasound beams using the ultrasound probe;

sequentially display each of the plurality of ultrasound images on the monitor;

detect an excrement region, which is a region where excrement is likely to be present, from each of the plurality of ultrasound images;

specify a presence or absence of the excrement by detecting the excrement region from one or more ultrasound images among the plurality of ultrasound images based on a detection result of the excrement region;

highlight-display the excrement region in each of the plurality of ultrasound images sequentially displayed on the monitor in a case where it is specified that the excrement is present; and notify a user of a message suggesting a change of an approach of the ultrasound probe during performing the scanning in a case where it is not specified that the excrement is present within a predetermined period, wherein the processor further detects excrement property information of the excrement region from each of the plurality of ultrasound images, the processor further specifies an excrement property of the excrement region based on the excrement property information, the processor highlight-displays the excrement region in each of the plurality of ultrasound images sequentially displayed on the monitor in a case where it is specified that the excrement is present and the excrement property is specified, and the processor notifies a user of a message suggesting a change of the approach in a case where it is not specified that the excrement is present within the predetermined period or in a case where it is specified that the excrement is present but the excrement property is not specified, and wherein the processor detects, for each of the plurality of ultrasound images, a statistic value of brightness in the excrement region, and the processor obtains, for each of the plurality of ultrasound images, a first comparison result by comparing the statistic value of brightness in the excrement region with a third threshold value, and specifies the excrement property based on one first comparison result in the first ultrasound image or a plurality of first comparison results in the plurality of ultrasound images, or the processor detects, for each of the plurality of ultrasound images, a brightness ratio between the statistic value of brightness in the excrement region and a statistic value of brightness in a predetermined region around the excrement region, and the processor obtains, for each of the plurality of ultrasound images, a second comparison result by comparing the brightness ratio with a fourth threshold value, and specifies the excrement property based on one second comparison result in the first ultrasound image or a plurality of second comparison results in the plurality of ultrasound images.

25. An ultrasound diagnostic apparatus comprising:

an ultrasound probe;

a monitor; and a processor, wherein the processor is configured to:

sequentially generate a plurality of ultrasound images based on a reception signal obtained by scanning an examination area of a subject with ultrasound beams using the ultrasound probe;

sequentially display each of the plurality of ultrasound images on the monitor;

detect an excrement region, which is a region where excrement is likely to be present, from each of the plurality of ultrasound images;

specify a presence or absence of the excrement by detecting the excrement region from one or more ultrasound images among the plurality of ultrasound images based on a detection result of the excrement region;

highlight-display the excrement region in each of the plurality of ultrasound images sequentially displayed on the monitor in a case where it is specified that the excrement is present; and notify a user of a message suggesting a change of an approach of the ultrasound probe during performing the scanning in a case where it is not specified that the excrement is present within a predetermined period, wherein the processor further detects excrement property information of the excrement region from each of the plurality of ultrasound images, the processor further specifies an excrement property of the excrement region based on the excrement property information, the processor highlight-displays the excrement region in each of the plurality of ultrasound images sequentially displayed on the monitor in a case where it is specified that the excrement is present and the excrement property is specified, and the processor notifies a user of a message suggesting a change of the approach in a case where it is not specified that the excrement is present within the predetermined period or in a case where it is specified that the excrement is present but the excrement property is not specified, and wherein the processor detects, for each pixel of each of the plurality of ultrasound images, a probability that each pixel is included in each of classes of the excrement properties, determines, among the classes of the excrement properties, a class having a highest probability as a class of each pixel, and detects, as the excrement region, a collection of the plurality of pixels that are determined as pixels of the excrement based on the class of each pixel, and the processor obtains a total area of the classes for each of the classes of the excrement properties, and specifies a class having a largest total area, as the excrement property of the excrement region.

* * * * *